US00PP30769P2

(12) United States Plant Patent
Hansen

(10) Patent No.: US PP30,769 P2
(45) Date of Patent: Jul. 30, 2019

(54) ***HOSTA* PLANT NAMED 'DIAMOND LAKE'**

(50) Latin Name: ***Hosta* hybrid (Tratt.)**
Varietal Denomination: Diamond Lake

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 15/998,208

(22) Filed: Jul. 13, 2018

(51) Int. Cl.
*A01H 5/12* (2018.01)

(52) U.S. Cl.
USPC ..... Plt./353

(58) Field of Classification Search
USPC ..... Plt./353
CPC ..... A01H 5/02; A01H 5/12; A01H 5/0272; A01H 6/12; A01H 6/56
See application file for complete search history.

*Primary Examiner* — June Hwu

(57) ABSTRACT

A new and distinct *Hosta* plant named 'Diamond Lake' with large rounded-mound habit of dense, cordate foliage of heavy glaucous bluish-colored above and whitish-blue below, retaining the glaucous covering until the end of summer; Leaves have deeply impressed veins with moderate dimpling between the veins and sinuate margins. The plant has lavender flowers densely arranged on arching bluish-colored scapes above the foliage.

1 Drawing Sheet

Latin name and variety denomination of the plant:
Botanical classification: *Hosta* hybrid (Tratt.).
Variety denomination: 'Diamond Lake'.

FEDERALLY SPONSORED RESEARCH

This invention was developed without any federally sponsored research or development funding.

BACKGROUND AND ORIGIN OF THE PLANT

The present invention relates to a new and distinct *Hosta* plant, *Hosta* 'Diamond Lake' hereinafter also referred to as the new plant or the cultivar name, 'Diamond Lake'. *Hosta* 'Diamond Lake' was hybridized at a wholesale nursery in Zeeland, Mich., USA in the summer of 2011 as a cross between two unreleased proprietary hybrids known as H9-310 (not patented) and H9-57 (not patented) as the female and male parents, respectively. The new plant is the selection of as a single seedling among several in that cross identified as 11-397-1 through the trial process. The new plant has been asexually propagated by division at the same nursery in Zeeland, Mich., USA since 2014, and also by careful plant shoot-tip tissue culture, with the resultant asexually propagated plants having retained all the same traits as the original plant.

No plants of *Hosta* 'Diamond Lake' have been sold, under this or any other name, in this country or anywhere in the world, prior to the filing of this application, nor has any disclosure of the new plant been made prior to the filing of this application with the exception of that which may have been sold or disclosed within one year of the filing date of this application and was either derived directly or indirectly from the inventor.

BRIEF SUMMARY OF THE PLANT

There are over 5,800 registered *Hosta* cultivars with The American *Hosta* Society, which is the International Cultivar Registration Authority for the genus *Hosta* along with a similar number of unregistered cultivars. The nearest comparison cultivars known to the inventor are 'Neptune' U.S. Plant Pat. No. 19,674, 'Blue Angel' (not patented), 'Waterslide' (U.S. Plant Pat. No. 30,303), and 'Queen of the Seas' (not patented).

'Neptune' is smaller in habit and leaf size, the leaves are narrower, have a more narrowly acute apex, more arching, have less substance than that of the new plant. 'Blue Angel' has more cordate and less rounded foliage with less glaucous blue, the habit is slightly larger and the scapes are much taller. 'Waterslide' is smaller in leaf size and habit with more narrow foliage and less dimpling between the veins. 'Queen of the Seas' is more upright in habit with smaller foliage having less glaucous blue foliage and less dimpling. The female parent, H9-310 a hybrid comprising 'Niagara Falls' (not patented), is larger in habit and foliage with green foliage having ruffled sinuate leaf margin, and the male parent, H9-57 (a cross of 'Neptune' times 'Fulda' (not patented)), is smaller in habit and foliage with longer deltoid-shaped, intense glaucous blue foliage with very ruffled sinuate margins.

Other *Hosta* cultivars have glaucous foliage, but 'Diamond Lake' is distinct from the above listed *Hostas* and all other cultivars known to the discoverer by the following combined traits:

1. Large rounded-mound plant habit with dense foliage;
2. Cordate foliage with sinuate margins, small sharply pointed apices and cordate base;
3. Leaves with heavy glaucous bluish coloring above and glaucous whitish-blue below retained until the end of the summer;
4. Leaves have deeply impressed veins and are moderately dimpled between the veins;
5. Tightly-compact lavender flowers on arching glaucous bluish-colored scapes above foliage.

BRIEF DESCRIPTION OF THE DRAWINGS

The photographs of the new plant demonstrate the overall appearance of the new plant, including the unique traits. The colors are as accurate as reasonably possible with color reproductions. Ambient light spectrum, temperature, source and direction may cause the appearance of minor variation in color.

DETAILED BOTANICAL DESCRIPTION

Figure 1:
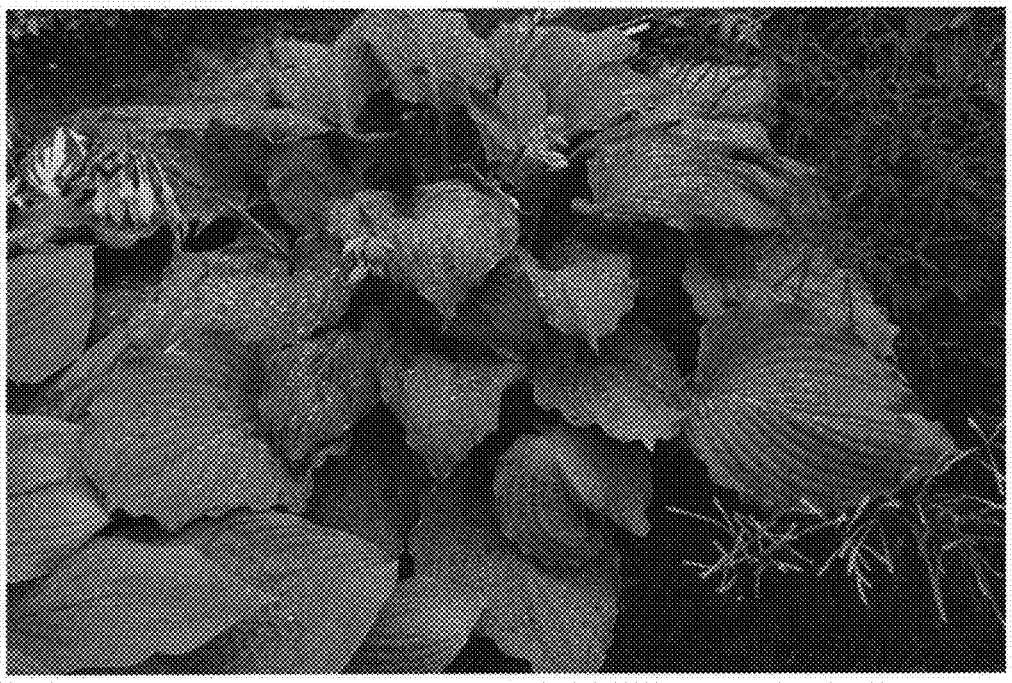
FIG. 1 shows a top view of a seven-year-old plant showing plant habit.
Figure 2:
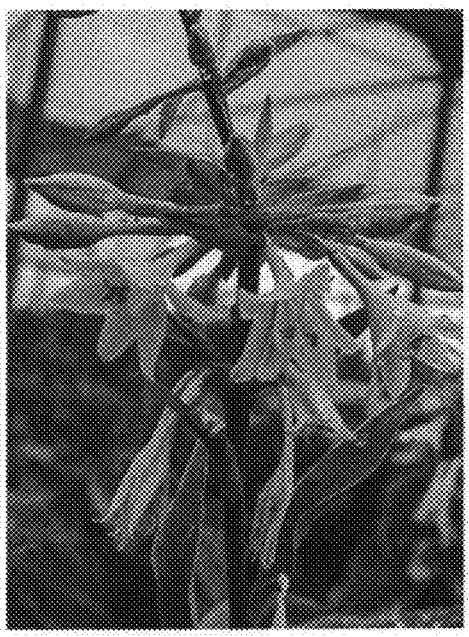
FIG. 2 shows a close-up of the flowering scape.
Figure 3:
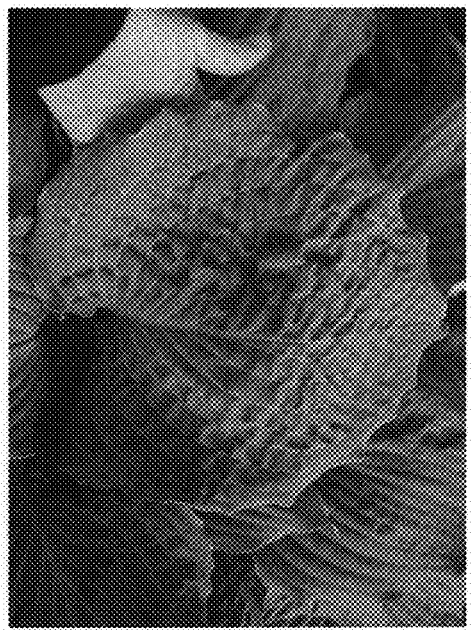
FIG. 3 shows a leaf demonstrating sinuate margins, impressed veins, dimpling between veins and glaucous surface.

The following descriptions and color references are based on the 2015 edition of The Royal Horticultural Society Colour Chart except where common dictionary terms are used. The new plant, *Hosta* 'Diamond Lake', has not been observed under all possible environments. The phenotype may vary slightly with different environmental conditions, such as temperature, light, fertility, moisture and maturity levels, but without any change in the genotype. The following observations and size descriptions are of a seven-year old plant in a partially shaded trial garden in Zeeland, Mich. with supplemental water and fertilizer.

Botanical classification: *Hosta* x hybrid;

Parentage: Hybrid of H9-310 as the female parent, and H9-57 as the male parent;

Propagation: Garden division and sterile shoot-tip tissue culture;

Time to initiate roots from tissue culture: About two to three weeks;

Growth rate: Rapid;

Crop time: About 10 to 12 weeks to finish during the summer in a one-liter container from rooted tissue culture plantlet;

Rooting habit: Normal, fleshy, lightly branching; color nearest RHS NN155B depending on soil type;

Plant shape and habit: Hardy herbaceous perennial with basal rosette of leaves emerging from rhizomes producing a large symmetrical upright, rounded-mound of leaves;

Plant size: Foliage height about 60.0 cm above soil line to the top of the leaves and about 175.0 cm wide at the widest point slightly above the soil line;

Foliage description: Glabrous, heavily glaucous abaxial and adaxial; cordate, with acute to apiculate apex and cordate base; margin entire and sinuate; with dimples between the veins; blades generally flat, without twisting;

Leaf blade size: To about 33.0 cm long, 26.0 cm wide near base; average about 22.5 cm long, 30.5 cm wide;

Leaf blade color: Early season and shortly after emerging adaxial nearest RHS 137A and abaxial nearest RHS 190A; mid-season and later summer adaxial nearest blend between RHS N138A and RHS 189B; mid-season and later abaxial blend between RHS N138D and RHS 189B;

Petiole: Entire, glabrous, glabrous, concavo-convex; mostly straight from base of plant to leaf base with little bending or curving, strong but flexible; to about 48.0 cm long and 14.0 mm wide at base;

Petiole color: Adaxial center nearest blend of RHS 138B and RHS 137B toward margin; abaxial center nearest RHS 145C and margin nearest RHS N138B;

Veins: Parallel, impressed adaxial or moderately bulging or costate on abaxial side; typically 13 to 14 pairs and one main center vein;

Veins color: Adaxial midrib blend of RHS 138B and RHS 137B with secondary veins nearest RHS 147D; abaxial midrib nearest RHS 145C and secondary veins blend between RHS 191C and RHS 148C;

Flower description:

Buds one day prior to opening: Clavate with acute apex and narrow tubular base; entire bud about 48.0 mm long, with swollen distal portion about 13.0 mm diameter and about 30.0 mm long, base tube about 18.0 mm long and about 3.5 mm diameter; flowers slightly smaller distally;

Bud color: Base tube between RHS 85C and RHS 85D; apical swollen portion with alternating petals of nearest RHS 85D for inner petals and RHS 85C for outer petal set;

Flowers: Perfect; single; actinomorphic; funnelform; held slightly drooping to outwardly; about 18.0 mm wide and 65.0 mm long; fused in basal 35.0 mm; corolla to about 57.0 mm long and 18.0 mm wide at apex, tube portion about 20.0 mm long and 3.0 mm diameter (distal flowers smaller); persists for a normal period, usually one day on plant or as cut flower; scapes remain effective with flowers beginning early July for about four weeks in Michigan; about 50 flowers per scape; held in compact whorls and individually;

Floral bracts: Subtending individual flowers; lanceolate, acute apex, truncate clasping base; to about 38.0 mm long and 18.0 mm wide, decreasing distally; concavo-convex;

Floral bract color: Adaxial blend between RHS 146D and RHS 138B with heavy tinting on veins and lighter between veins of nearest RHS 187A; abaxial more glaucous than adaxial, nearest RHS N138C with slight tinting on veins and between veins of nearest RHS 187A;

Flower fragrance: None detected;

Tepal: Six; typically two sets of three, glabrous, entire; oblanceolate with acute apex and fused base; both sets long length, approximately 57.0 mm long and about 14.0 mm wide about 5.0 mm above fusion;

Tepal color: Adaxial inner set nearest RHS 85C with three veins nearest RHS 85A, clear margins and white portion about 0.5 mm wide of nearest RHS NN155D between center and clear margins and tube; adaxial outer set nearest RHS 85C with three veins nearest RHS 85A and white margin about 0.5 mm wide and tube nearest RHS NN155D; abaxial inner set between RHS 85C and RHS 85D with nearest RHS 85C in tube; abaxial outer set between RHS 85C and RHS 85D in bulb with apical 1.0 mm nearest RHS 147C and tube nearest RHS 85C;

Gynoecium: Single; tri-carpelled; 67.0 mm long; exserted;

*Style*.—Single; terete; approximately 61.0 mm long, 0.7 mm diameter, arcuate upward about 90 degrees in distal 10.0 mm; color base nearest RHS 2D, distally nearest 155A.

*Stigma*.—Globose, micro-puberulent; about 1.2 mm in across and 1.0 mm tall; color nearest RHS 155A.

*Ovary*.—Oblong, fluted; about 5.0 mm long and 2.0 mm diameter at widest; rounded apex and truncate base; color nearest RHS N144D.

Androecium:

*Filaments*.—Typically six; terete; approximately 66.0 mm long and 0.7 mm in diameter; arcuate upward about 90 degrees in the apical 10.0 mm; color base nearest RHS 2D, nearest RHS 155A distally.

*Anthers*.—Elliptic; dorsifixed, longitudinally dehiscent; about 6.0 mm long and 2.5 mm wide; color adaxial nearest blend of RHS 170B and RHS 161A, abaxial nearest RHS 155A with micro-speckles in distal half of nearest RHS 187A.

*Pollen*.—Abundant; elliptic, less than 0.1 mm long; color nearest RHS 13A.

Peduncle: Terete; usually one per mature division and thirteen per plant; glaucous, glabrous; slightly drooping to outwardly; to about 90.0 cm tall, and about 8.0 mm in diameter at base; average about 80.0 cm and 7.5 mm diameter, flowering portion about 30.0 cm long;

Peduncle color: When flowering nearest RHS 137B without glaucous bloom and a nearest RHS 191C with glaucous bloom;

Pedicel: Glabrous; glaucous; terete; secund, slightly curved downwardly; approximately 10.0 mm long and 1.5 mm diameter, decreasing in size distally;

Pedicel color: Distal portion nearest RHS 85A, proximally nearest RHS 138D;

Fruit: Oblong ellipsoid, with apiculate apex; tri-valved dehiscent capsule; about 35.0 cm long and 7.0 mm diameter; color when mature nearest RHS 161C;

Seed: Typically about 30 to 39 viable seeds per capsule; endospermic; flattened-elliptic wing surrounding embryo situated toward one end of ellipse; about 11.0 mm long and 4.0 mm wide at wing; embryo portion about 5.0 mm long, 3.0 mm wide and 1.5 thick; color nearest RHS 202A;

Disease tolerance and resistance: The new plant has not shown any resistance to pests and diseases common to *Hostas*. The plant grows best and shows best coloration with plenty of moisture, adequate drainage and light shade, but is able to tolerate some drought when mature, and tolerates direct sun without leaf burn, especially during the cooler parts of the day and when provided sufficient water. Hardiness at least from USDA zone 3 through 9, and other disease resistance is typical of that of other *Hostas*.

It is claimed:

1. A new and distinct ornamental plant cultivar named *Hosta* 'Diamond Lake' as herein described and illustrated.

* * * * *